United States Patent
Davis et al.

(10) Patent No.: US 6,367,637 B1
(45) Date of Patent: *Apr. 9, 2002

(54) INSTRUMENT ORGANIZER WITH MOVABLE STABILIZING POST

(75) Inventors: Phillip Davis, Weston; Vito L. DiPinto, South Windsor, both of CT (US)

(73) Assignee: General Hospital Supply Corporation, Wilton, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/515,284

(22) Filed: Feb. 29, 2000

(51) Int. Cl.[7] .............................. A47F 7/00; A47F 5/10
(52) U.S. Cl. ................. 211/85.13; 211/70.6; 211/184; 211/13.1
(58) Field of Search .................. 211/85.13, 43, 211/70.6, 184, 13.1; 206/370

(56) References Cited

U.S. PATENT DOCUMENTS

| | | | | |
|---|---|---|---|---|
| 4,229,420 A | * | 10/1980 | Smith et al. ................ | 422/310 |
| 4,342,391 A | * | 8/1982 | Schainholz ................ | 206/370 |
| 4,512,466 A | * | 4/1985 | Delang ........................ | 206/370 |
| 4,641,749 A | * | 2/1987 | Link et al. .................. | 206/370 |
| 4,865,821 A | * | 9/1989 | Langdon ..................... | 422/300 |
| 5,046,624 A | * | 9/1991 | Murphy et al. ............ | 211/70.6 |
| 5,072,835 A | * | 12/1991 | Price et al. .................. | 211/40 |
| 5,145,655 A | * | 9/1992 | Darlak ........................ | 422/300 |
| 5,201,430 A | * | 4/1993 | Artzer ......................... | 211/70.6 |
| 5,657,702 A | * | 8/1997 | Ribeyrolles ................. | 108/61 |
| 5,664,691 A | * | 9/1997 | Boivin-Paradis ............ | 211/184 |
| 6,048,503 A | * | 4/2000 | Riley et al. ................. | 422/298 |

OTHER PUBLICATIONS

Medical Action Industries, Inc. Product literature (3 pages) regarding Ancillary Products, no date.

Contour Fabricators of Florida, Inc. Product Literature (2 pages) regarding Disposable Medical Surgical Products, no date.

Graphic Controls Corporation Product Brochure, (8 pages)© 1998.

DC Medical, Division of PSC Corporation Product Literature (single page), no date.

* cited by examiner

Primary Examiner—Gregory J. Strimbu
(74) Attorney, Agent, or Firm—Law Office of Roger C. Phillips

(57) ABSTRACT

A movable stabilizing structure for use with an instrument organizer including an elongated base having a uniform, predetermined width and fixed posts extending upwardly from the base. The movable stabilizing structure includes two gripping legs with opposing, inwardly facing surfaces spaced-apart a distance substantially equal to the predetermined width of the base of the organizer, so that the opposing, inwardly facing surfaces of the two gripping legs will grip opposite sides of the base of the organizer so that the movable stabilizing structure can be attached to the base at any point between the fixed posts of the organizer and held in place by the gripping legs to help maintain instruments in an organized and upright state on the organizer.

14 Claims, 1 Drawing Sheet

INSTRUMENT ORGANIZER WITH MOVABLE STABILIZING POST

BACKGROUND OF THE DISCLOSURE

1. Field of the Disclosure

The present disclosure relates, in general, to an organizer with a stabilizing post for separating and securing surgical instruments, e.g., before and during surgery, and in preparation for sterilization. More particularly, the present disclosure relates to a movable stabilizing post for separating, securing and maintaining surgical instruments in an upright position on an instrument organizer.

2. Background of the Related Art

Surgical instruments, such as hemostats, scissors, forceps, etc., are normally separated and organized during surgical procedures and before being sterilized by being laid in an upright position on rolled-up cotton towels. The rolled-up cotton towels, which may have their outside edges taped, support the instruments such that the instruments can be more easily counted, selected and handled by a doctor or nurse during a surgical procedure, or while the instruments are assembled prior to sterilization.

Foam organizers have also been provided to support and group surgical instruments before and during actual use of the instruments. Such organizers can have an elongated base with fixed posts extending upwardly from ends of the base. The foam organizers support the instruments, with the instruments resting on the base and leaning against the posts, such that the instruments can be more easily counted, selected and handled by a doctor or nurse during a surgical procedure, or while the instruments are assembled prior to sterilization.

Such rolled cotton towels or foam organizers, with the surgical instruments supported thereon, are usually laid out on a tray or a table. Sometimes, however, before and during use of the surgical instruments, the instruments supported on the rolled towel or the organizer can topple over from their upright positions and become mixed and disorganized and, accordingly, more difficult to count, select and handle prior to actual use of the instruments, or while the instruments are assembled prior to sterilization. In addition, it is not uncommon for the cotton towels to produce lint, which can transmit microorganisms and result in contamination of the surgical instruments.

What is needed, therefore, is a means for retaining surgical instruments in an organized and/or upright position on an instrument organizer. What is also needed is an improved instrument organizer, wherein, instruments supported thereon are less likely to topple over from an upright position prior to actual use or sterilization of the instruments and are, therefore, easier to count, select and handle. What is additionally needed is an improved instrument organizer having means for securing the organizer to a surface, such as on a tray or a table top for example, so that the organizer will not move while supporting instruments. Preferably, the improved instrument organizer will be lint-free.

SUMMARY OF THE DISCLOSURE

Accordingly, a movable stabilizing post is provided for use with an instrument organizer including an elongated base having a uniform, predetermined width and fixed posts extending upwardly from the base. The movable stabilizing post has two gripping legs with opposing, inwardly facing surfaces that are spaced-apart a distance substantially equal to the predetermined width of the base of the organizer. The opposing, inwardly facing surfaces of the two gripping legs, therefore, grip opposite sides of the base of the organizer so that the movable stabilizing post can be attached to the base at any point between the fixed posts of the organizer and held in place by the gripping legs to help maintain the instruments in an organized and upright state.

According to one aspect of the present disclosure, both the instrument organizer and the movable stabilizing post are made of lint-free foam plastic. According to another aspect of the present disclosure, both the instrument organizer and the movable stabilizing post are non-sterile and disposable. According to a further aspect of the present disclosure, the instrument organizer is provided with an adhesive strip on a bottom surface thereof for securing the organizer to a surface, such as a tray or table top for example.

Still other features and advantages of the presently disclosed surgical instrument organizer and method for sterilizing surgical instruments will become apparent upon reading the following detailed description in conjunction with the attached drawings.

As used herein, the term "self-gripping legs" refers to legs that, by themselves, grip and maintain a hold on a base sufficient to support implements such as surgical instruments in an upright manner.

DETAILED DESCRIPTION OF THE DISCLOSURE

Figure 1:
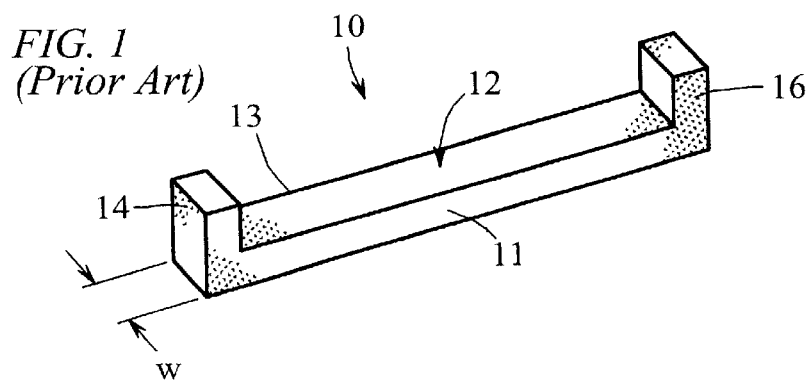
FIG. 1 shows a perspective view of a prior art instrument organizer for supporting surgical instruments within a surgical tray.

Referring to FIG. 1, an existing surgical instrument organizer 10 is shown. The organizer is used for supporting and helping to organize surgical instruments, e.g., before and during actual use of the instruments and/or in preparation for sterilization of such instruments. The organizer 10 includes an elongated base 12 having front and rear surfaces 11, 13 spaced a uniform predetermined width "w" and fixed end posts 14, 16 a extending upwardly from ends of the base.

Although not shown, surgical instruments, such as hemostats, scissors, forceps, etc., can be supported by the organizer 10 such that the instruments can be organized into separate groups and more easily selected and handled by a doctor or nurse during a surgical procedure and when assembling instruments prior to sterilization. The instrument organizer 10 is used in place of a rolled-up cotton towel.

Figure 2:
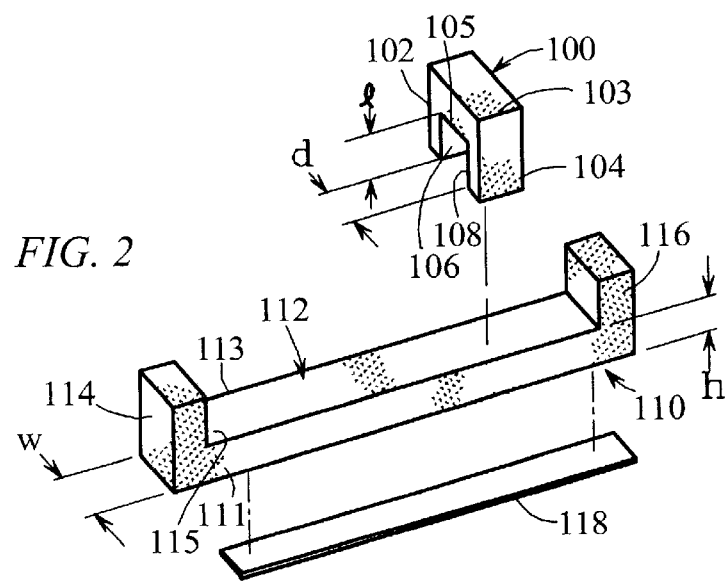
FIG. 2 shows an exploded perspective view of an instrument organizer, including a movable stabilizing post according to the present disclosure and a self-adhesive strip.
Figure 3:
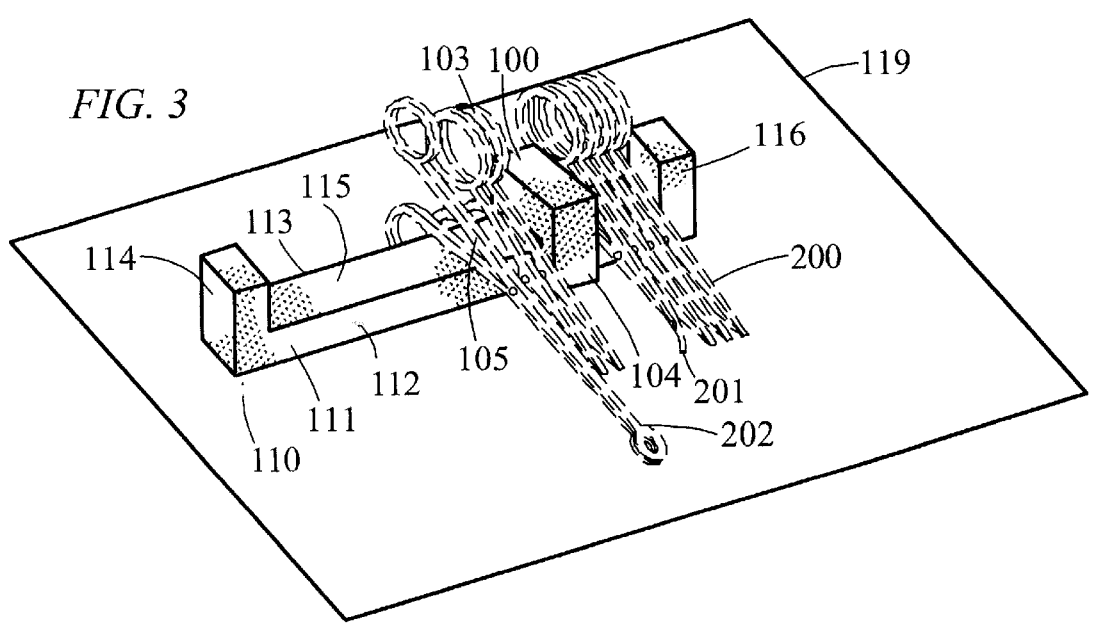
FIG. 3 shows a perspective view of the instrument organizer of FIG. 2 disposed on a planar support and, in turn, supporting surgical instruments in an upright position, with the movable stabilizing post secured to the organizer and providing support to the instruments.

Referring to FIGS. 2 and 3, a movable stabilizing post 100 according to the present disclosure is shown being used with an instrument organizer 110 similar to the instrument organizer 10 of FIG. 1. The movable stabilizing post 100 provides the benefit of maintaining instruments supported by the organizer in an organized and upright manner to ensure that the instruments can be more easily organized, counted, selected and handled by a doctor or nurse during a surgical procedure, or when assembling instruments prior to sterilization, and enhances an operating team's assurance that the surgical instruments will be lint-free.

The movable stabilizing post 100 includes two gripping legs 102, 104 extending downwardly from a central body that defines a post 103, and having spaced-apart, opposing, inwardly facing surfaces 106, 108. The opposing, inwardly facing surfaces 106, 108 of the gripping legs 102, 104 of the movable stabilizing post 100 are spaced apart a distance "d" substantially equal to the predetermined width "w" of the base 112 of the organizer 110.

The movable stabilizing post 100, therefore, is fit on the base 112 of the organizer 110 so that the opposing, inwardly facing surfaces 106, 108 of the gripping legs 102, 104 of the movable stabilizing post 100 may solely grip the front and rear surfaces 111, 113 of the base, whereby the movable stabilizing post can be attached to the base of the organizer at any point between the fixed end posts 114, 116 and be retained in place at that point by the gripping legs. Preferably, a length "l" of the gripping legs 102, 104 is either not greater than or is equal to a height "h" of the base 112 of the organizer 110 so that a bottom surface 105 of the post 103 of the moveable stabilizing post 100 contacts a top surface 115 of the base 112 to provide additional stability. Preferably, as illustrated, the movable stabilizing post is formed from material such that the post 103 includes exterior surfaces which are generally planar and integral with corresponding exterior surfaces of the gripping legs 102, 104.

As shown in FIG. 3, the movable stabilizing post 100 can be positioned on the base 112 of the organizer 110 which is, in turn, disposed on a planar support surface 119. Use of the movable stabilizing post 100, insures that surgical instruments 200, 201, 202 will be maintained in an upright position against one of the fixed end posts 116 of the organizer. The movable stabilizing post 100 prevents instruments, partially supported on the organizer 110 and partially supported on planar support surface 119, from toppling over from their upright positions and becoming mixed and disorganized. The improved organization and accessibility provided by the organizer/stabilizing post find particular utility before and during a surgical procedure, and/or in preparation for sterilization.

Preferably, the organizer 110 and the movable stabilizing post 100 are both made of a non-woven, non-absorbent, lint-free material. The organizer 110 and the movable stabilizing post 100 are preferably made of a lint-free foam plastic. In addition, it is envisioned that the organizer 110 and the movable stabilizing post 100 can be provided in a sterile state.

Referring in particular to FIG. 2, the organizer 110 can also be provided with a double-sided adhesive strip 118 on a bottom surface of the base 112 of the organizer. The adhesive strip 118 allows the organizer 110 to be secured to a planar support surface 119, such as a tray or table top for example, to hold the organizer in place and further prevent surgical instruments supported thereon from toppling over and becoming disorganized. The adhesive strip 118 may further be provided in a sterile state.

The principles, preferred embodiments and modes of operation of the presently disclosed instrument organizer and movable stabilizing post have been described in the foregoing specification. The presently disclosed instrument organizer and movable stabilizing post, however, are not to be construed as limited to the particular embodiments shown, as these embodiments are regarded as illustrious rather than restrictive. Moreover, variations and changes may be made by those skilled in the art without departing from the spirit and scope of the instrument organizer and movable stabilizing post and disclosed herein and recited in the appended claims.

What is claimed is:

1. An instrument organizer for at least partially supporting surgical instruments, comprising:
    an elongated base having a uniform, predetermined width and defining a continuous surface extending from a first side surface to an opposing second side surface thereof, the elongated base including two terminal ends;
    at least one fixed post extending from one of said terminal ends of the base; and
    at least one movable stabilizing structure including two self-gripping legs extending generally parallel to each other and from a central body of the stabilizing structure, the self-gripping legs each having an inwardly facing surface, the inwardly facing surfaces being opposed to one another and spaced-apart a distance substantially equal to the predetermined width of the base of the instrument organizer, the opposing, inwardly facing surfaces of the two self-gripping legs being dimensioned and configured to solely grip the first and second side surfaces of the base of the instrument organizer, so that the movable stabilizing structure is attachable to the base of the instrument organizer and the central body is held in place by the self-gripping legs for retaining the surgical instruments in an organized and upright state partially on the organizer; and wherein:
    the central body of the movable stabilizing structure includes an upwardly extending post comprising a first side surface and a second side surface that each define a plane that extends in a direction that is generally perpendicular to a longitudinal axis of the elongated base when the movable stabilizing structure is mounted to the elongated base;
    each self-gripping leg of the movable stabilizing structure including a first side surface and a second side surface each of which defines a plane that also extends in the direction that is generally perpendicular to the longitudinal axis of the elongated base when the movable stabilizing structure is mounted to the elongated base; and
    the plane defined by the first side surface of the upwardly extending post and the planes defined by the first side surfaces of the self-gripping legs are generally coplanar and the plane defined by the second side surface of the upwardly extending post and the planes defined by the second side surfaces of the self-gripping legs are generally coplanar.

2. An instrument organizer according to claim 1, wherein a height of the elongated base is greater than a length of each of the self-gripping legs such that a bottom surface of the central body will engage the continuous surface of the elongated base.

3. An instrument organizer according to claim 1, wherein a height of the elongated base is approximately equal to a length of each of the self-gripping legs such that a bottom surface of the central body will engage the continuous surface of the elongated base.

4. An instrument organizer according to claim 1, wherein the elongated base is composed of a lint free foam plastic and is dimensioned and configured to support only one end of the surgical instruments, the elongated base being dimensioned and configured to be mounted on a planar support surface that supports another end of the surgical instruments.

5. An instrument organizer according to claim 1, wherein the fixed post comprises two said fixed posts extending upwardly from terminal ends of the elongated base.

6. An instrument organizer according to claim 1, wherein said elongated base and said movable stabilizing structure are fabricated of a lint-free foam plastic.

7. An instrument organizer according to claim 1, further comprising a double sided self adhesive strip attached to a bottom surface of the elongated base.

8. An instrument organizer according to claim 7, wherein said double sided self-adhesive strip is sterile.

9. An instrument organizer comprising:

an elongated base structure having a top surface and a front surface and a rear surface extending from the top surface, and the front surface and the rear surface being disposed on opposing sides of the base structure, the elongated base structure comprising a predetermined width as measured from the front surface to the rear surface and the elongated base structure including opposed terminal ends;

at least one upstanding post fixedly positioned at one of said terminal ends of the base structure; and at least one movable stabilizing structure mountable at a location along a length of the base structure relative to said upstanding post, said movable stabilizing structure including a body portion and opposed, spaced apart self-gripping legs depending therefrom, said self-gripping legs each extending generally parallel to one another and to a respective one of said front and rear surfaces and being spaced apart a distance approximately equal to the predetermined width of the base structure and further being dimensioned and configured to facilitate frictional engagement solely with the front and rear surfaces of said base structure to thereby stabilize and support one or more surgical instruments in a generally upright state partially on the organizer; and wherein:

the body portion of the movable stabilizing structure includes an upwardly extending post comprising a first side surface and a second side surface that each define a plane that extends in a direction that is generally perpendicular to a longitudinal axis of the elongated base structure when the movable stabilizing structure is mounted to the elongated base structure;

each self-gripping leg of the movable stabilizing structure including a first side surface and a second side surface each of which defines a plane that also extends in the direction that is generally perpendicular to the longitudinal axis of the elongated base structure when the movable stabilizing structure is mounted to the elongated base structure; and the plane defined by the first side surface of the upwardly extending post and the planes defined by the first side surfaces of the self-gripping legs are generally coplanar and the plane defined by the second side surface of the upwardly extending post and the planes defined by the second side surfaces of the self-gripping legs are generally coplanar.

10. An instrument organizer according to claim 9, wherein the elongated base structure comprises a generally rectangular shape in cross section.

11. An instrument organizer accordingly to claim 9, wherein the elongated base structure is composed of a material that is insufficiently rigid to support the surgical instruments, the elongated base being dimensioned and configured to be mounted on a planar support surface that provides a necessary additional support for the surgical instruments.

12. An instrument organizer comprising:

an elongated base structure having a top surface and a front surface and a rear surface extending from the top surface, and the front surface and the rear surface being disposed on opposing sides of the base structure, the elongated base structure comprising a predetermined width as measured from the front surface to the rear surface and the elongated base structure including opposed terminal ends;

at least one upstanding post fixedly positioned at one of the terminal ends of the base structure; and at least one movable stabilizing structure comprising a body portion and self-gripping means extending away from the body portion and having at least a portion of which engage the front and rear surfaces of the base structure, for stabilizing and supporting at least one sugical instrument in a generally upright state at least partially on the organizer and the self-gripping means having a length that is not greater than a height of the base structure.

13. An instrument organizer according to claim 12, wherein the elongated base structure is dimensioned and configured to support only one end of the surgical instrument, the elongated base structure also being dimensioned and configured to be mounted on a planar support surface which supports another end of the surgical instrument.

14. An instrument organizer according to claim 12, wherein:

the body portion includes an upwardly extending post comprising a first side surface and a second side surface that each define a plane that extends in a direction that is generally perpendicular to a longitudinal axis of the elongated base structure when the movable stabilizing structure is mounted to the elongated base structure;

the self-gripping means comprises a pair of self-gripping legs that each include a first side surface and a second side surface each of which defines a plane that also extends in the direction that is generally perpendicular to the longitudinal axis of the elongated base structure when the movable stabilizing structures mounted to the elongated base structure; and the plane defined by the first side surface of the upwardly extending post and the planes defined by the first side surfaces of the self-gripping legs are generally coplanar and the plane defined by the second side surface of the upwardly extending post and the planes defined by the second side surfaces of the self-gripping legs are generally coplanar.

* * * * *